United States Patent
Mauclaire

(10) Patent No.: US 10,285,782 B2
(45) Date of Patent: May 14, 2019

(54) DENTAL APPLIANCE FOR CONSTRAINING THE TONGUE

(75) Inventor: Claude Mauclaire, Troyes (FR)

(73) Assignee: TONGUE LABORATORY LIMITED (GB)

( * ) Notice: Subject to any disclaimer, the term of this patent is extended or adjusted under 35 U.S.C. 154(b) by 0 days.

(21) Appl. No.: 13/057,141

(22) PCT Filed: Aug. 6, 2009

(86) PCT No.: PCT/EP2009/060226
§ 371 (c)(1),
(2), (4) Date: Jun. 3, 2011

(87) PCT Pub. No.: WO2010/015685
PCT Pub. Date: Feb. 11, 2010

(65) Prior Publication Data
US 2011/0262881 A1    Oct. 27, 2011

Related U.S. Application Data

(60) Provisional application No. 61/086,684, filed on Aug. 6, 2008.

(30) Foreign Application Priority Data

Aug. 6, 2008    (FR) .................................... 08 55452

(51) Int. Cl.
*A61C 7/00*    (2006.01)
*A61F 5/56*    (2006.01)

(52) U.S. Cl.
CPC ................ *A61C 7/00* (2013.01); *A61F 5/566* (2013.01)

(58) Field of Classification Search
CPC .. A61C 7/08; A61C 7/10; A61C 5/566; A61C 7/00; A61F 5/50; A61F 5/56; A61F 5/556; A61F 5/58; A61F 2005/563
USPC ...... 433/6–7, 18–24, 140; 128/848, 859–862
See application file for complete search history.

(56) References Cited

U.S. PATENT DOCUMENTS

| | | | |
|---|---|---|---|
| 3,162,948 A | 12/1964 | Gerber | |
| 4,471,771 A * | 9/1984 | Brown | ................. A61F 5/0006 128/859 |
| 5,052,409 A | 10/1991 | Tepper | |

(Continued)

FOREIGN PATENT DOCUMENTS

| | | |
|---|---|---|
| DE | 195 03 288 C1 | 7/1996 |
| DE | 100 11 687 A1 | 11/2000 |

(Continued)

OTHER PUBLICATIONS

"Unitek MIA Quad Helix System". 3M Unitek 1999.*

(Continued)

*Primary Examiner* — Edward Moran
(74) *Attorney, Agent, or Firm* — Merchant & Gould P.C.

(57) ABSTRACT

A dental appliance includes an attachment mechanism suited to attach the appliance on the teeth of a patient's upper jaw. The appliance includes a constraining mechanism linked to the attachment mechanism, where the constraining mechanism is suited to limit the movement of a central zone of the tongue and allow the anterior and lateral edges of the patient's tongue to perform movements necessary for speech and swallowing.

17 Claims, 3 Drawing Sheets

(56) References Cited

U.S. PATENT DOCUMENTS

| | | | | |
|---|---|---|---|---|
| 5,376,001 | A | * 12/1994 | Tepper | A61C 7/00 433/6 |
| 5,816,800 | A | * 10/1998 | Brehm | A61C 7/10 433/20 |
| 5,871,350 | A | * 2/1999 | Clark | A61C 7/00 433/18 |
| 6,033,216 | A | * 3/2000 | Souris | A61C 7/10 433/18 |
| 2001/0027793 | A1 | 10/2001 | Tielemans | |
| 2009/0126742 | A1 | 5/2009 | Summer | |
| 2011/0284011 | A1 | 11/2011 | Mauclaire | |

FOREIGN PATENT DOCUMENTS

| | | |
|---|---|---|
| WO | WO 2006/125216 A2 | 11/2006 |
| WO | WO 2010/015685 A1 | 2/2010 |

OTHER PUBLICATIONS

Dentaurum, "Wire appliances, rapid palatal expansion (RPE) appliances: The tongue shield for meialisation". Feb. 15, 2008, accessed via Internet Archive Wayback Machine at http://www.o-atlas.de/eng/kapitel6_181.php.*

International Search Report and Written Opinion for Application No. PCT/EP2009/060226 dated Nov. 13, 2009.

International Search Report and Written Opinion for Application No. PCT/IB2011/003268 dated May 14, 2012.

Stahl F, Grabowski R, Gaebel M & Kundt G (2007) Relationship between occlusal findings and orofacial myofunctional status in primary and mixed dentition. Part II: Prevalence of orofacial dysfunctions. J. Orofac. Orthop. 68: 74-90 (2007).

* cited by examiner

DENTAL APPLIANCE FOR CONSTRAINING THE TONGUE

CROSS REFERENCE TO RELATED APPLICATIONS

This application is a National Stage Application of PCT/EP2009/060226, filed 6 Aug. 2009, which claims benefit of Serial No. 0855452, filed 6 Aug. 2008 in France, and which also claims benefit of Ser. No. 61/086,684, filed 6 Aug. 2008 in the United States and which applications are incorporated herein by reference. To the extent appropriate, a claim of priority is made to each of the above disclosed applications.

BACKGROUND OF THE INVENTION

The field of the invention is that of dental appliances. Orthodontic devices such as a Quad Helix are known in the art as devices that can be attached to the molars by two bands, and have four active helix springs. These orthodontic devices can correct certain pathologies such as widening the arch of the mouth to make room for crowded teeth, or correcting a posterior cross-bite, where lower teeth are buccal (outer) than upper teeth. However, the inventor has observed that medicine does not adequately take into account the role of the tongue in the occurrence of various pathologies.

The tongue is an assembly of 17 muscles. Because of untimely and unceasing action, some of these muscles develop excessively giving the tongue a significant volume, greater than the volume considered to be "normal," considering the size of the buccal cavity of the patient in question. The condition is known as macroglossia.

Macroglossia has at its origin poor habits often acquired in childhood at an age at which the child must stop sucking and learn to chew, speak and swallow when its first teeth emerge. This learning of new reflexes, if it is acquired incorrectly, leads to an exaggerated use of certain muscles of the tongue. The tongue builds muscle in a manner that is unbalanced and excessive. The tongue progressively enlarges and because of its volume can disrupt the respiratory tracts, pharynx, hypopharynx, etc. The tongue serves to remodel all the adjoining structures of the buccal cavity such as the palate, nasal fossae, jaw, etc.

Macroglossia can have varied and sometimes serious consequences. For example, it is often the cause of pathological snoring and sleep apnea, which affect many people and are manifest as an obstruction of the respiratory airways with more or less frequent stoppages of respiration, leading among other things to poor oxygenation during sleep. Beyond the consequences in the patient's daily life (disturbing others by snoring and/or presenting with fatigue, somnolence, memory loss, cardiac disorders, etc.), this poor oxygenation can lead, in severe cases, to the patient's death. Sleep apnea appears to be a cause for many cases of sudden infant death.

The resting position of the tongue, even without macroglossia is also very important, The high resting position of the tongue hollows the palate, which correspondingly reduces the volume of the nasal fossae and blocks the pharynx. Consequently, the soft palate height increases. This can lead to reduced respiration through the nose and forced respiration through the mouth, which seems to play a role in allergic rhinitis and even in asthma because dust (pollen, asbestos, etc.) arrives directly in the airways, since the air is not filtered by the nose.

Macroglossia dysfunction and resting position of the tongue are also at the origin of many osseous and dental malformations and deformations such as upper and lower prognathia and labioversion (rabbit teeth, spaces between the teeth, etc.), Down's syndrome hanging tongue, protruding lower jaw, open bite between the upper and lower jaws, narrow and deep palates, and even loosening of the teeth.

The existing techniques for reducing macroglossia are essentially based on surgery. But, the results obtained by these techniques are short-lived and relapses are frequent. Among the causes of these failures is that the necessary reeducation after surgical intervention is difficult to achieve, since the patient continues to perform incorrect movements of the tongue reflexively even after surgery.

SUMMARY OF THE INVENTION

An object of the invention is therefore to redress or attenuate these problems by proposing a device enabling reduction of macroglossia without need for surgery, and reeducation of a patient after surgery in order to avoid a relapse of macroglossia. This will provide normal function of the tongue, provide a good rest position of the tongue, and reduce the size of the tongue.

In one aspect of the invent ion is a dental appliance comprising (i) attachment means suited for attaching the appliance onto the teeth of the upper jaw of the patient, and (ii) constraining means linked to said attachment means, wherein the constraining means are adapted to limit the movement of a central zone of the tongue and to allow the anterior and lateral edges of the patient's tongue to perform movements necessary for speech and swallowing.

According to some embodiments of the invention, the appliance comprises one or more of the following features, taken individually or in a combination of two or more:

- The attachment means comprise at least two bands intended to be mounted respectively on two opposite molars of the upper jaw of the patient;
- The device comprises means of adjustment for the constraining means for the tongue;
- The constraining means comprises an arch arranged so that it comes in contact with the border of the central zone when the patient's mouth is closed;
- Each band comprises a sheath located on the palatal surface of the band, said sheath being suitable for receiving an end of the arch;
- The arch is formed of a metal wire;
- The means of adjustment comprise at least one loop or spiral formed by winding the metal wire on itself;
- The means of adjustment comprise two substantially vertical or slightly oblique loops or spirals each located in a substantially vertical plane, symmetrically about the sagittal plane, to enable the adjustment of the height of the anterior section of the arch;
- The means of adjustment comprise one or two substantially horizontal loops or spirals placed in the anterior section of the arch to enable the adjustment of the width of the anterior section of the arch;
- The appliance comprises additional means of support intended to avoid movements of the attachment means;
- The additional support means comprise two stems of metal wire, where one end of each stem is rigidly connected to a means of attachment and each stem is suited to be positioned against an edge of the palate located near the palatal surfaces of the teeth in the upper jaw;

The end of each stem is rigidly connected to a band and is attached thereto by means of said sheath;

Advantageously, the dental appliance according to the invention can be used in a method for treating obstructive sleep apnea comprising attaching the appliance on the upper jaw of a patient suffering from dysfunction or a bad resting position of the tongue, and adjusting the device so as to constrain the patient's tongue in a set position corresponding to a normal resting position of the tongue.

The invention visually resembles a Quad Helix, but the design and effect are fundamentally different. A Quad Helix is designed for adapting to the palate and changing its size, either enlarging or reducing it. The Quad Helix is designed to correct for bilateral molar expansion and bilateral expansion of the jaw arch, molar rotation, torque and tipping, expansion of the canines and premolars, and correction of crossed occlusions. The Quad Helix is an appliance which exerts a significant lateral force on the maxillaries by use of four horizontal coils. The Quad Helix is set vertically on the molars which is necessary for placing it and activating it either when contracting or expanding; it must be adjusted to the palate for being the least bothersome possible, and be able to exert a horizontal force on the osseous parts of the palate and its sutures. The outlet of the Quad Helix system of attachment to the bands initially is director towards the rear of the mouth, and thereafter follows the vertical osseous wall of the palate, with the first coil horizontal and the symmetric one from the other side of the palate allowing the desired expansion of the palate and the dental articulation. The Quad Helix does not have vertical coils.

In contrast, the present device has two vertical coils for acting from top to bottom and two horizontal coils for adapting to the width of the palate. The arch of the present device is free in the occlusal area and is directed towards the tongue rather than the palate or any osseous structure. Vertical coils are provided to adjust the height relative to the tongue. This permits the present device to restrict movement of the tongue, which is a function that the Quad Helix is not designed to perform.

BRIEF DESCRIPTION OF THE DRAWINGS

The invention and its advantages will be better understood upon reading the following description, given solely as an example, and made in reference to the attached drawings, in which.

DETAILED DESCRIPTION OF THE PREFERRED EMBODIMENT

Figure 1:
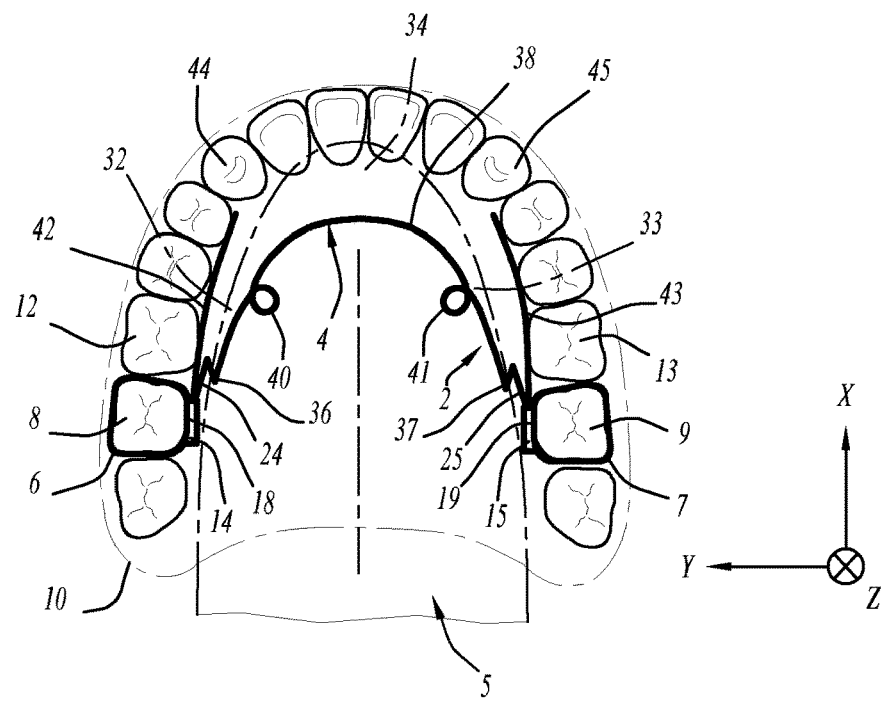
FIG. 1 is a schematic view from below of an upper jaw bearing the dental appliance according to the invention.

Following is a description of a preferred embodiment of the dental appliance according to the invention while the appliance is in functional position in the buccal cavity 1 of the patient.

Generally, the orientation of the FIGS. 1 to 5 is given by an XYZ reference frame. The x-axis corresponds to the patient's sagittal axis oriented from back to front, the y-axis corresponds to the transverse axis oriented from the patient's left to right, and the z-axis is the medial longitudinal axis, positioned substantially vertically when the patient is in the basic anatomic position, where the z-axis is oriented from bottom to top.

The dental appliance 2, used for constraining the tongue in a set position corresponding to a normal resting position, comprises an arch 4 suited for contacting the patient's tongue 5 for limiting the movements thereof, attachment bands 6 and 7 for keeping the appliance 2 in position on the patient's upper jaw, and an additional means of support for stabilizing the appliance 2 during its use.

The bands, respectively right 6 and left 7, are suited for tightening on the second molars, respectively right 8 and left 9, of the patient's upper jaw 10. As a variant, the bands 6 and 7 are arranged on the first molars 12 and 13 of the upper jaw 10. For example, this is the case of children in whom the second molars are not yet emerged.

Figure 3:
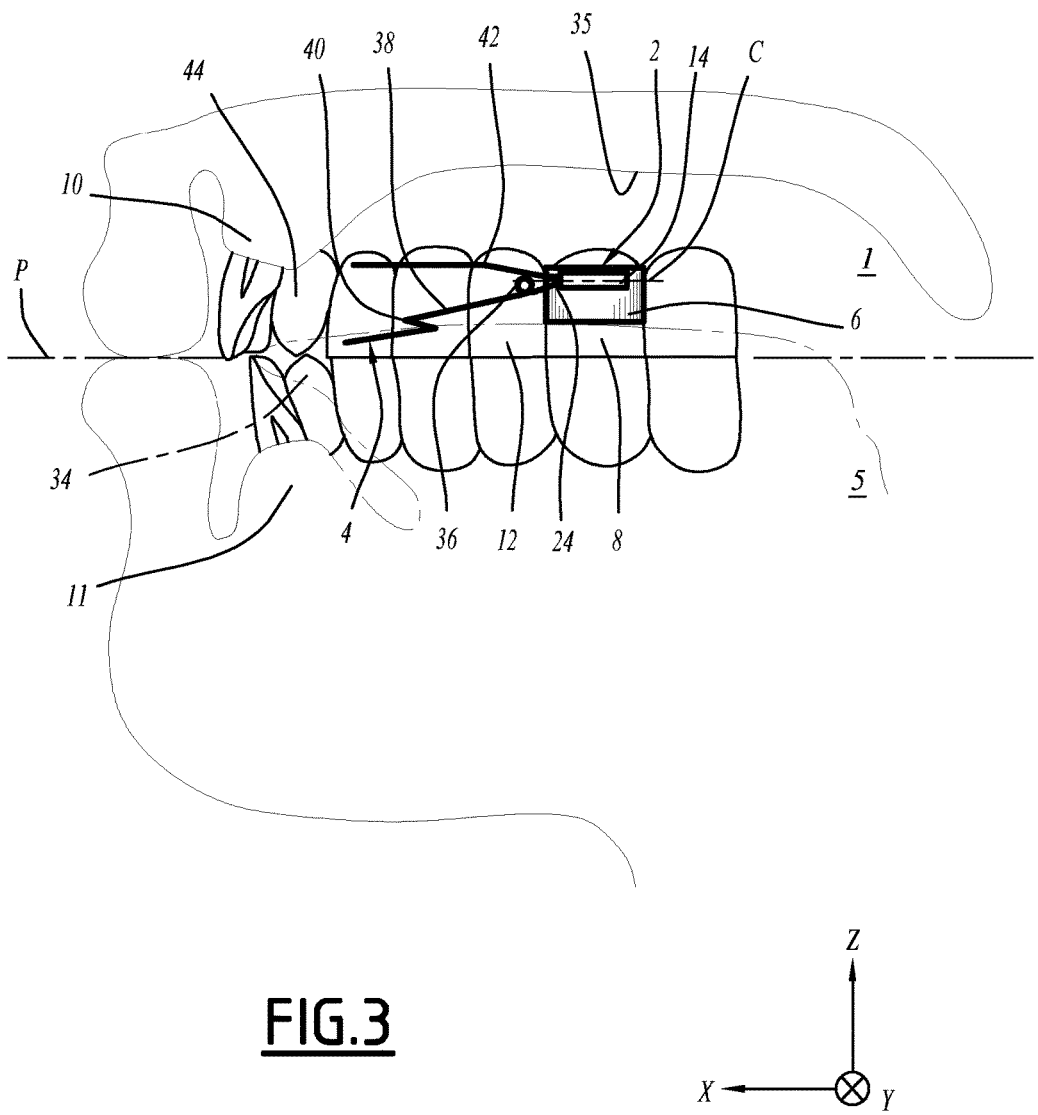
FIG. 3 is a sagittal section of the buccal cavity of the patient wearing the dental appliance from FIG. 1.

Each band 6, respectively 7, is provided with a sheath whose section is substantially rectangular 14, 15, which for example has dimensions of 2 mm×2.5 mm and a length of order 4 mm. Such horizontal lingual sheaths are for example sold by the U.S.A. company Rocky Mountain Orthodontics with catalog number A0186. Each sheath 14, 15 is for example welded on a palatal surface 18, 19 of the band 6, 7 where the palatal surface is a surface oriented towards the inside of the buccal cavity 1. As shown in FIG. 3, the axis C of the sheath 14, respectively sheath 15, is in a substantially horizontal plane and very close to the occlusion plane P of the patient's jaws.

The arch 4 is formed from metal wire, for example an 0.036" diameter "Elgiloy blue" type wire, sold by the American company Rocky Mountain Orthodontics. Each of the ends 24 and 25 of the arch 4 is received in the sheath 14, 15 of each of the bands 6 and 7.

Figure 2:
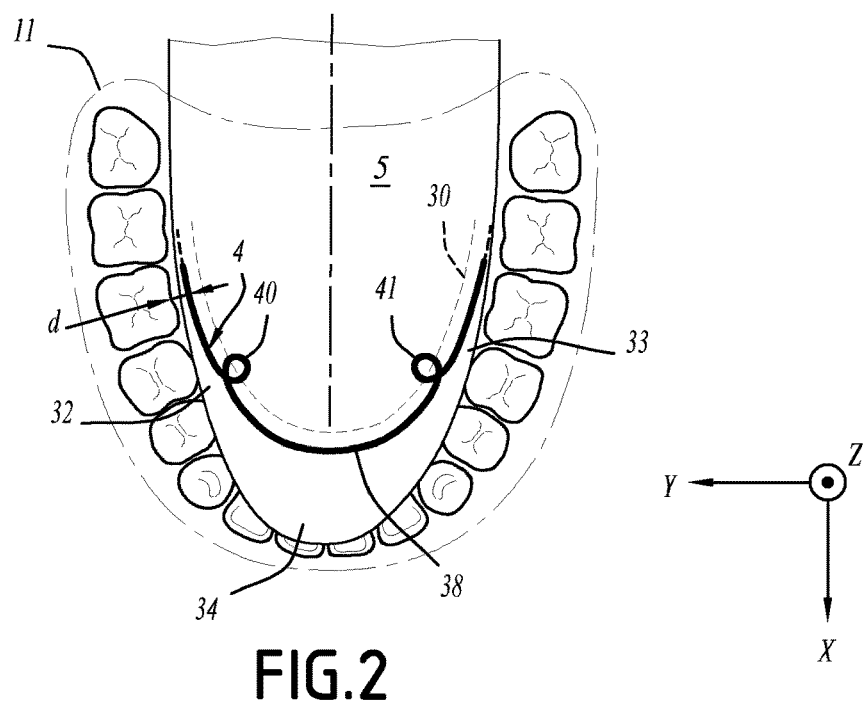
FIG. 2 is a schematic view from above of a lower jaw illustrating the functioning position of the dental appliance arch from FIG. 1 relative to the patient's tongue.

Seen from above, as illustrated in FIG. 2, the arch 4 is shaped to come in contact with the border 30 of the central zone of the patient's tongue 5, when the patient's mouth is closed so as to limit the movements of the central zone of the tongue. At the same time, the right lateral edge 32, the left lateral edge 33 and the forward edge or tip 34 of the tongue 5 can still make the movements necessary for speech or swallowing. The arch 4 follows, at a distance d when the range between 1 cm and 0.5 cm, the arch formed by the palatal surfaces of the teeth of the lower jaw 11.

In sagittal section, as FIG. 3 shows, the arch 4 is located in the area of the plane of occlusion P. It should be noted that the arch 4 is away from the palate 35 of the buccal cavity 1 of the patient.

The arch 4 comprises means of adjustment of the geometry thereof enabling an adaptation of the appliance 2 to the specific shape of the mouth of the patient.

The means of adjustment comprise predominantly vertical or slightly oblique loop 36 and 37 on both sides of the sagittal plane and near sheathes 14 and 15. Each vertical loop, 36 and 37, is made by forming a loop by winding the metal wire constituting the arch 4 on itself through 360°.

When the appliance 2 is in functional position in the patient's mouth, the vertical loops 36 and 37 are located in a substantially vertical plane, parallel to the XZ-plane, and directed upward. The vertical loops 36 and 37 make it possible for the dental professional to elastically deform the metal wire of the arch 4 to incline the anterior section 38 of the arch 4 more or less relative to the plane of occlusion P, i.e., in a controlled manner.

The means of adjustment also comprise two substantially horizontal right 40 and left 41 loops placed symmetrically along the anterior section 38, on both sides of the XZ sagittal plane, about 1 cm forward from each of the vertical loops 36 and 37. The distance separating the two horizontal loops 40 and 41 varies depending on the width of the patient's buccal cavity and is generally from 2 to 3 cm. Each horizontal loop, 40 and 41, is made by forming a loop by winding the metal wire constituting the arch 4 on itself. The horizontal loops 40 and 41 enable the plastic deformation of the metallic wire constituting the arch 4 in order to adapt the shape of the arch 4 to the geometry of the patient's dentition and to the shape of the border 30 of the central zone of the tongue 5 with which the arch 4 comes in contact. Further, the horizontal loops 40 and 41 provide an additional contact surface between the arch 4 and the tongue 5 and make it possible to spread the palate if it is too narrow, and improve the nasal respiration.

The appliance 2 preferably comprises an additional means of support. Actually, when the tongue 5 exerts forces on the arch 4, these forces, amplified because of the lever arm, are exerted on the bands 6 and 7, through the sheath 14 and 15. To compensate for these significant forces which tend to move the bands 6 and 7, the appliance 2 is equipped with two stems, respectively right 42 and left 43, substantially straight. Each stem 42, 43 is constituted by a metal wire identical to that used for the arch 4. Each stem 42, 43 is attached at a first end to a band 6, 7 by insertion of this end in the sheath 14, 15 of this band. The stem 42, 43 extends from the band 14, 15 to which it is attached towards the front of the mouth 1, along the palatal surfaces of the upper jaw 10 pre-molars. The first end of the stem 42, 43 is located in the area of the canine 44, 45. The stem 42, 43 comes to rest on a relief of the upper jaw 10 located at the limit between the enamel of the teeth and the gum.

With this arrangement, when the bands 14, 15 are subject to forces which tend to pivot them around an axis parallel to the y-axis, the stems 42 and 43 come to rest on the relief of the upper jaw so as to generate forces which oppose the pivoting of the bands 6 and 8.

For greater rigidity, the first end of the stem and the end of the arch housed in the same sheath are welded together. As a variant, a stem is made by folding the metal wire constituting the arch 4 back on itself, where the portion folded back is housed in the attachment sheath. The end of the stem is curved and attaches the device to the ring to prevent it from coming out of the sheath of the ring.

In another embodiment, the arch for constraining the tongue is removable. The means for keeping the arch on the bands are consequently also adapted. For example, the palatal surface of an attachment band is provided with an element forming a sheath placed vertically, such as a Wilson 3D lingual tube with catalog number A4114 from Rocky Mountain Orthodontics, and with which combined means provided on the corresponding end of the arch engage by insertion.

Still as a variant, the vertical loops are replaced by loops arranged obliquely. Such loops enable both a height and width adjustment of the arch. It is then possible to dispense with providing the arch with horizontal loops.

The positioning of the appliance which was just described is done as follows.

The dental professional tightens the bands 6 and 7 on each of the two first molars 8 and 9 of the patient's upper jaw 10.

The dental professional next lodges the ends of the arch 4 and the stems 36 and 38 in the sheaths 14 and 15 and deforms them to assure the hold by tightening. Then, using pliers, the dental professional deforms the various horizontal 40 and 41 and vertical 36 and 37 loops of the arch 4 for adapting in width and height the geometry of the arch 4 to the patient's buccal cavity. In its functional position, the arch 4 is adjusted a little above the desired position of the tongue, which is a normal resting position in which the tongue is relaxed and located near the dental arch of the lower jaw, just behind the lower incisors, without exerting any force on them.

At the end of the adjustment, the arch 4 is such that it leaves a sheath, downward and forward, while separating from the palatal surface of the teeth in the upper jaw so as to not interfere with the occlusion. The arch 4 is deformed so as to come into contact about 0.5 cm from the outer edge of the tongue 5. The arch 4 is therefore not arranged against the patient's palate 35, but in the space between the upper and lower arches of the patient's buccal cavity.

Then the stems forming the additional supports are placed along the palatal surfaces of the premolars, near the neck of the teeth, meaning in the area of the junction of the teeth with the gums.

Thus positioned, the appliance 2 acts by only allowing the tongue 5 the movements necessary for its normal function, meaning articulation of the dental sounds (T, D, N) and L, and the evacuation of the alimentary bolus by swallowing.

When the tongue 5 moves in a prohibited manner, the border 30 of the central zone meets the arch 4, which forms an obstacle. Thus, the sucking movement becomes impossible and so do other undesirable movements. To avoid injury by rubbing on the metal wire and the horizontal loop, the tongue "learns," through a reflex mechanism, to avoid certain movements and to try to remain calm.

The appliance according to the invention opposes the undesirable acquired habits and hinders the function of the tongue during the first days of treatment. Progressively, the tongue is re-educated so as to function properly, within the constraints of the present device. In about three months, a consequent reduction of the volume of the tongue is observed. To limit the number of relapses, the appliance is advantageously worn for about six months. If the dental professional wishes to remodel the shape of the tongue, the appliance will be worn longer, as the horizontal branches are separated along the premolars. During the treatment, the dental professional can modify the position of the arch, for example to further lower it towards the tongue.

By moving less, some muscles of the tongue are less stressed and consequently, over time, their volume is reduced.

By blocking the tongue from pressing against the palate, the tongue remains in a low and relaxed position. The respiratory paths are progressively freed. The tongue no longer blocks the oropharynx.

The palate is remodeled and becomes less deep while also widening, which increases the volume of the nasal fossae and improves nasal respiration.

Since respiration is made easier, sleep apnea and snoring disappear. The patient then recovers a deep sleep and better quality of life, without recourse to a surgical technique.

The implementation of the appliance also helps improve articulation of words possible, because the presence of the appliance promotes use of the lips.

Figure 4:
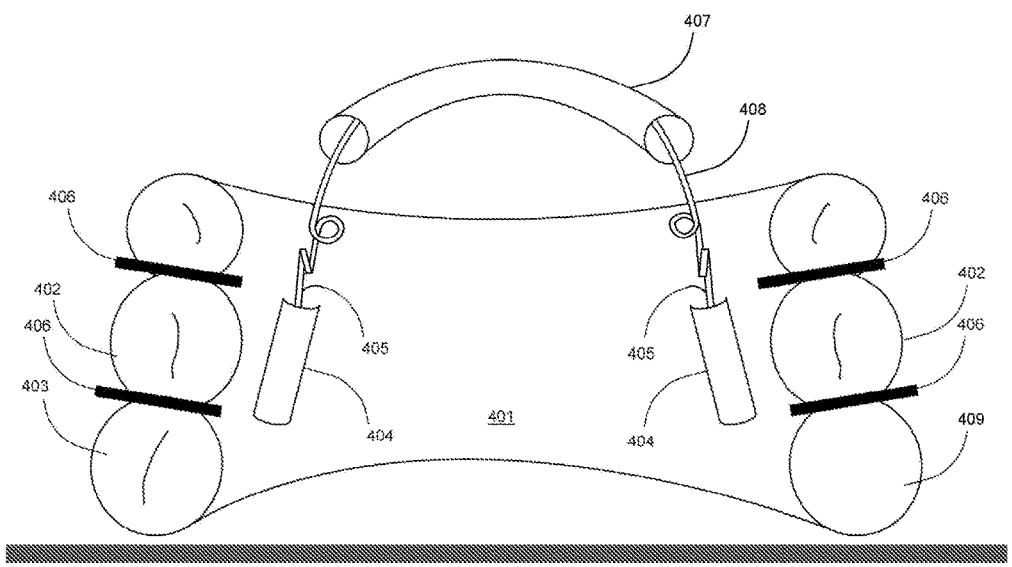
FIG. 4 is a schematic view from below of an upper jaw bearing another embodiment of the dental appliance according to the invention.

In another embodiment, particularly suitable for patients missing one or more molars, e.g., because of a tooth extraction, the means of constraint are made by a metal wire arch set in a resin plate adapted to the palatal arch. Referring to FIG. 4, this embodiment comprises a small thin resin plate 401 which covers the bottom of the palate and is held in place by the force of suction between the bottom of the palate and the resin plate 401, wherein the shape of the resin plate 401 is adapted to the palatal arch. Thin resin plate 401 may also be held in place by at least two hooks 406 on each side of the upper jaw, which grip one or more available teeth, such as teeth 402, 403. Position 409 indicates a missing tooth, and FIG. 4 illustrates hooks 406 grip the teeth that are adjacent to position 409. On the side of the teeth opposite from sleeve 404, hooks 406 may be joined together by a cross-member, or may remain separate. Two sleeves 404, one on each side, are affixed by a process such as autopolymerization onto the thin resin plate 401 parallel to the teeth 402, 403. The ends of the appliance 405 are inserted into sleeves 404, and may be secured to sleeves 404 by a mechanical attachment such as threading, friction, or other methods known in fastening arts for this purpose. The appliance may include a sheath 407 around metal wire arch 408, the sheath 407 providing greater comfort to a user than a bare metal wire arch without a sheath.

Figure 5:
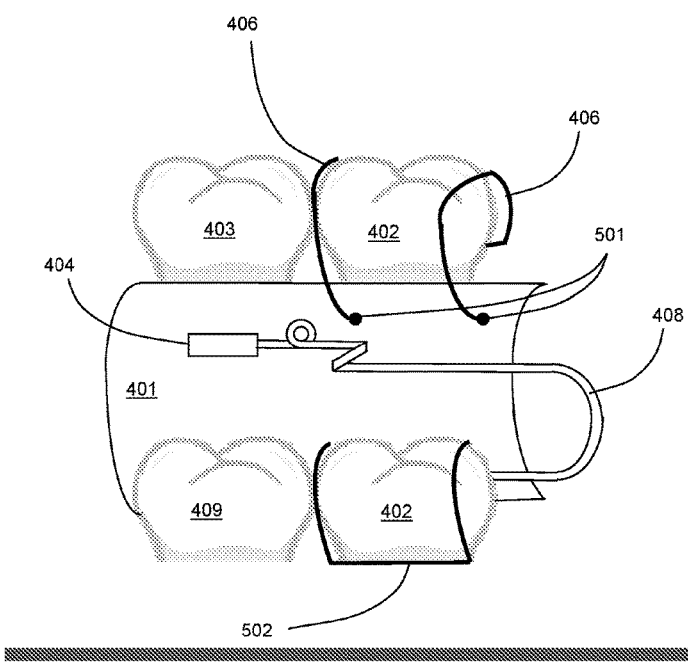
FIG. 5 is a perspective view from below of a portion of the embodiment of FIG. 4.

FIG. 5 illustrates a detailed perspective view of a portion of the embodiment of FIG. 4, wherein hooks 406 are attached to thin resin plate 401 at anchor points 501, one anchor point 501 per hook 406. Optional cross-member 502 connects two adjacent hooks 406 to provide additional stability.

The invention claimed is:

1. Dental appliance comprising:
an attachment mechanism adapted to attach the appliance onto molars of an upper jaw of a patient; and
a constraining mechanism linked to said attachment mechanism, wherein the constraining mechanism includes an arch including posterior end portions linked to the attachment mechanism and an anterior portion adapted, when the attachment mechanism is attached to the molars of the upper jaw of the patient, to be located at a border of a central zone of a tongue of the patient, the border being spaced apart from palatal surfaces of teeth of a lower jaw of the patient, the arch being positioned spaced apart from a palate of the patient, the arch limiting the movement of an anterior part of the central zone of the tongue toward the palate of the patient and allowing anterior and lateral edges of the tongue to perform movements necessary for speech and swallowing, the constraining mechanism further including an adjustment mechanism to adjust the constraining mechanism, the adjustment mechanism including a first pair of loops and a second pair of loops, wherein the arch is sized and positioned such that, when the attachment mechanism is attached to the molars of the upper jaw of the patient, both the first pair of loops and the second pair of loops are positioned anterior relative to the attachment mechanism, wherein portions of the arch posterior to both the first and second pairs of loops and extending from the attachment mechanism towards the first pair of loops are angled towards an occlusal plane of the patient, and a portion of the arch anterior to both the first and second pairs of loops is positioned to approach the occlusal plane of the patient relative to the attachment mechanism.

2. The appliance as claimed in claim 1, wherein said attachment mechanism comprises at least two bands tightenable respectively on two opposite molars of the upper jaw of the patient.

3. The appliance as claimed in claim 1, wherein the arch is arranged so that the arch is adapted to come in contact with the border of the central zone of the tongue when a mouth of the patient is closed.

4. The appliance as claimed in claim 2, wherein each of the at least two bands comprises a horizontal sheath located on a lingual surface of the band, wherein each said sheath receives one end of the arch, and wherein both the first pair of loops and the second pair of loops are positioned anterior relative to each of the horizontal sheaths.

5. The appliance as claimed in claim 3, wherein the arch comprises a metal wire.

6. The appliance as claimed in claim 5, wherein each of the loops is formed by winding the metal wire on itself.

7. The appliance as claimed in claim 6, wherein each of the first pair of loops is substantially vertical or slightly oblique, each of the first pair of loops being located in a substantially vertical plane, symmetrically about a sagittal plane, to enable adjustment of a height of the anterior portion of the arch.

8. The appliance as claimed in claim 6, wherein each of the second pair of loops is substantially horizontal and located in the anterior portion of the arch to enable the adjustment of a width of the anterior portion of the arch.

9. The appliance as claimed in claim 1, further comprising an additional support mechanism to prevent movement of the attachment mechanism.

10. The appliance as claimed in claim 9, wherein said additional support mechanism comprises two stems of metal wire, wherein one end of each stem is substantially rigidly connected to the attachment mechanism and each stem is adapted to be positioned against an edge of the palate located near palatal surfaces of teeth in the upper jaw.

11. The appliance as claimed in claim 10, wherein an end of each stem is substantially rigidly connected to a band of the attachment mechanism, and is attached thereto by a sheath.

12. The appliance as claimed in claim 7, wherein each of the second pair of loops is substantially horizontal and located in the anterior portion of the arch to enable the adjustment of a width of the anterior portion of the arch, and wherein a distance between one of the substantially vertical or slightly oblique loops and one of the substantially horizontal loops is approximately one molar of the patient in length.

13. The appliance as claimed in claim 1, wherein the attachment mechanism is configured to attach the appliance onto opposite molars of an upper jaw of the patient, the opposite molars corresponding to first or second molars of the upper jaw of the patient.

14. The appliance as claimed in claim 1, wherein the first pair of loops and the second pair of loops appear as closed loops when viewed from at least one perspective.

15. The appliance as claimed in claim 1, wherein the anterior portion of the arch comprises an apex of the arch, which, when the attachment mechanism is attached to the molars of the upper jaw of the patient, extends forward of the attachment mechanism and approaching the occlusal plane relative to the attachment mechanism, and wherein when the attachment mechanism is attached to the molars of the upper jaw of the patient, the apex of the arch is positioned above the occlusal plane of the patient and spaced apart posteriorly from incisors of the upper jaw of the patient.

16. A dental appliance comprising:
an attachment mechanism to attach the appliance onto molars of an upper jaw of a patient; and a constraining mechanism linked to said attachment mechanism, wherein the constraining mechanism includes an arch including an anterior portion, which, when the attachment mechanism is in place and attached to the molars of the upper jaw of the patient, is located at a border of a central zone of a tongue of the patient, the border being spaced apart from palatal surfaces of teeth of a lower jaw of the patient, the arch being positioned above the tongue of the patient, the arch spaced apart from a palate of the patient and limiting the movement of an anterior part of the central zone of the tongue toward the palate of the patient and allowing anterior and lateral edges of the tongue to perform movements necessary for speech and swallowing, the constraining mechanism further including an adjustment mechanism to adjust the constraining mechanism, the adjustment mechanism including a first pair of loops and a second pair of loops, wherein the arch is sized and positioned such that, when the attachment mechanism is attached to the molars of the upper jaw of the patient, both the first pair of loops and the second pair of loops are positioned anterior relative to the attachment mechanism, wherein portions of the arch posterior to both the first and second pairs of loops and extending from the attachment mechanism towards the first pair of loops are angled towards an occlusal plane of the patient, and a portion of the arch anterior to both the first and second pairs of loops is positioned to approach the occlusal plane of the patient relative to the attachment mechanism.

17. A dental appliance comprising:
a rear end and a front end;
first and second bands;
a first sheath disposed on the first band and a second sheath disposed on the second band, the first sheath and the second sheath being positioned forward of the rear end of the dental appliance; and
a wire, a first portion of the wire being received in the first sheath and a second portion of the wire being received in the second sheath, the wire comprising:
 an arch having an apex, the apex being positioned between the first portion and the second portion of the wire, forward of the first and second bands, and forward of the first and second sheaths;
 a first pair of loops positioned forward of the first and second sheaths; and
 a second pair of loops positioned forward of the first pair of loops;
 wherein the arch is sized and positioned relative to the first and second bands such that, when the first and second bands are attached to molars of a patient, wherein portions of the arch rearwards of both the first and second pairs of loops and extending from the first and second sheaths towards the first pair of loops are angled towards an occlusal plane of the patient, and a portion of the arch forwards of both the first and second pairs of loops is positioned to approach the occlusal plane of the patient relative to the attachment mechanism, and such that the apex of the arch is above the occlusal plane of the patient and spaced apart rearwardly from incisors of an upper jaw of the patient.

* * * * *